United States Patent
Franzini et al.

(10) Patent No.: US 10,441,177 B2
(45) Date of Patent: *Oct. 15, 2019

(54) HIGH DEFINITION THERMAL IMAGING FOR MEDICAL APPLICATIONS

(71) Applicants: BAE Systems Information and Electronic Systems Integration Inc., Nashua, NH (US); Mark B. Lyles, Exeter, RI (US)

(72) Inventors: John R. Franzini, Hollis, NH (US); Mark B. Lyles, Exeter, RI (US); Robert H. Murphy, Lancaster, MA (US)

(73) Assignees: BAE Systems Information and Electronic Systems Integration Inc., Nashua, NH (US); Mark B. Lyles, Exeter, RI (US)

( * ) Notice: Subject to any disclaimer, the term of this patent is extended or adjusted under 35 U.S.C. 154(b) by 336 days.

This patent is subject to a terminal disclaimer.

(21) Appl. No.: 15/109,140

(22) PCT Filed: Aug. 7, 2015

(86) PCT No.: PCT/US2015/044233
§ 371 (c)(1),
(2) Date: Jun. 30, 2016

(87) PCT Pub. No.: WO2016/069086
PCT Pub. Date: May 6, 2016

(65) Prior Publication Data
US 2016/0317039 A1    Nov. 3, 2016

Related U.S. Application Data

(60) Provisional application No. 62/072,557, filed on Oct. 30, 2014.

(51) Int. Cl.
*G01N 25/72* (2006.01)
*H04N 5/44* (2011.01)
(Continued)

(52) U.S. Cl.
CPC ............ *A61B 5/015* (2013.01); *A61B 5/0077* (2013.01); *A61B 5/7203* (2013.01);
(Continued)

(58) Field of Classification Search
CPC ......... A61B 5/685; A61B 5/411; A61B 5/015; A61B 5/077
(Continued)

(56) References Cited

U.S. PATENT DOCUMENTS

2005/0143662 A1    6/2005    Marchitto et al.
2007/0058845 A1*   3/2007    Diakides ............... G06F 19/321
                                                              382/128
(Continued)

FOREIGN PATENT DOCUMENTS

WO    2015061128    4/2015

OTHER PUBLICATIONS

PCT/US2015/044233 International Search Report dated Nov. 18, 2015.
(Continued)

*Primary Examiner* — Jon Eric C Morales
(74) *Attorney, Agent, or Firm* — Scott J. Asmus

(57) ABSTRACT

An apparatus for high resolution thermal imaging in medical applications has a single channel EMI shielded sensor, remote cable, and laptop controller with real time image processing software. The apparatus provides high resolution, real-time viewable infrared (IR) images with a variable focus distance adjustable from six inches to infinity. The present invention enables crisp, clear imagery of the thermal band for greater awareness of everything within the field of
(Continued)

view. Various medical applications which would benefit from high resolution thermal imagery are presented.

15 Claims, 13 Drawing Sheets

(51) Int. Cl.
  *A61B 5/01* (2006.01)
  *A61B 5/00* (2006.01)
  *A61B 5/02* (2006.01)
(52) U.S. Cl.
  CPC .......... *A61B 5/02042* (2013.01); *A61B 5/445* (2013.01); *A61B 5/4504* (2013.01); *A61B 5/489* (2013.01); *A61B 5/725* (2013.01); *A61B 2562/18* (2013.01); *A61B 2576/00* (2013.01)
(58) Field of Classification Search
  USPC ....................................................... 600/474
  See application file for complete search history.

(56) References Cited

U.S. PATENT DOCUMENTS

| | | | |
|---|---|---|---|
| 2008/0161661 A1* | 7/2008 | Gizewski | A61B 5/0059 600/306 |
| 2009/0212218 A1 | 8/2009 | Hayashi et al. | |
| 2010/0041998 A1 | 2/2010 | Postel | |
| 2012/0037803 A1 | 2/2012 | Strickland | |
| 2013/0329054 A1 | 12/2013 | Hoelter et al. | |
| 2014/0081133 A1 | 3/2014 | Nie et al. | |
| 2015/0004837 A1* | 1/2015 | Brichard | H01R 24/30 439/607.41 |
| 2016/0058377 A1* | 3/2016 | Butte | A61B 5/411 600/474 |

OTHER PUBLICATIONS

White et al., "Digital IR Imaging Capability for Medical Applications", Proceedings Optical Diagnostics of Living Cells II, vol. 3712, Jul. 13, 1999, pp. 35-46. Orlando, FL.

Altman et al., "Lockheed Martin's 640x480 Uncooled Microbolometer Camera", Proceedings Optical Diagnostics of Living Cells II, vol. 3698, Jul. 26, 1999, p. 137. Orlando, FL.

Kubala et al., "Increasing the Depth of Field in an LWIR System for Improved Object Identification", Proceedings Optical Diagnostics of Living Cells II, vol. 5784, May 12, 2005, p. 146. Orlando, FL.

Diakides, "Medical Applications of IR Focal Plane Arrays", Advanced Concepts Analysis Inc., Falls Church, VA. Mar. 15, 1998, pp. 2, 5 and 11. Fort Belvoir, VA.

SPIE Europe Ltd., "ULIS and BAE Systems Push Thermal Imaging Performance", Jun. 17, 2014, p. 1.

Kumar et al., "Fixed Pattern Noise Correction and Implementation for Infrared Focal Plane Array Based Staring System Using Scene Statistics", International Journal of Imaging Science and Engineering, Jan. 1, 2007, Figures 1, 2, 7 and p. 42.

Neo et al., "Naval Postgraduate School Monterey, CA Thesis", Fusion of Night Vision and Thermal Images Co-Advisors, Dec. 1, 2006, Figures 32, 33.

EPO Search Report, EP 15854988.1, dated Mar. 14, 2018. 17 pages.

* cited by examiner

HIGH DEFINITION THERMAL IMAGING FOR MEDICAL APPLICATIONS

CROSS-REFERENCE TO RELATED APPLICATIONS

This Application claims rights under 35 USC § 119(e) from U.S. Application Ser. No. 62/072,557 filed Oct. 30, 2014 the contents of which are incorporated herein by reference.

This application is related to the following applications, the contents of which are incorporated hereby by reference.

U.S. application Ser. No. 13/948,526 filed Jul. 23, 2013 entitled "CORRELATED CONTROL FOR CLOSE FOCUS STEREOSCOPIC VIEWING", PCT application PCT/US2014/060897 filed Oct. 16, 2014 entitled "MEDICAL THERMAL IMAGE PROCESSING FOR SUBCUTANEOUS DETECTION OF VEINS, BONES AND THE LIKE", U.S. application 62/046,195, filed Sep. 5, 2014 entitled "COMPACT MECHANISM FOR INTER-PUPIL DISTANCE ADJUSTMENT OF VIEWING SYSTEMS", and PCT application PCT/US15/44195 entitled "HIGH RESOLUTION INSPECTION DEVICE FOR CASTING DEFECTS USING IR" filed on even date herewith.

STATEMENT OF GOVERNMENT INTEREST

The invention was made with United States Government assistance under Contract No. H94003-04-D-0002/0105 awarded by the Department of the Navy. The United States Government has certain rights in this invention.

FIELD OF INVENTION

The present invention relates to high resolution IR imaging using the latest IR sensor technology combined with Real Time Image Processing algorithms. More particularly the invention relates to such imaging for medical applications.

BACKGROUND OF THE INVENTION

One of the problems with infrared sensors is the amount of electromagnetic interference which presents itself when an infrared camera is used to drive a conventional display, such as a laptop display. The result is oftentimes lines across the screen akin to what one would associate with analog television in a poor reception area. There is therefore a need to be able to provide an infrared camera system that is not susceptible to electromagnetic interference, so that when connected to a processor, for instance, in a laptop EMI interference is not present on the display screen.

Moreover, the type of infrared equipment used in medical laboratories is oftentimes cumbersome and heavy, not convenient enough for portable use. There is therefore a need for an infrared system for use in medical applications which can be carried in a suitcase, opened up and used at an off campus treatment site. Additionally, there is a need to process the output of a single channel infrared sensor to be able to sharpen up the image that is presented on-screen so that image resolution is high.

Thus, a heretofore unaddressed need exists in the industry to address the aforementioned deficiencies and inadequacies.

SUMMARY OF THE INVENTION

Embodiments of the present disclosure provide a system and method for high definition thermal imaging and close focus viewing from 6 inches to an infinite distance in medical applications. Briefly described, in architecture, one embodiment of the system, among others, can be implemented as follows. A device for high definition thermal imaging and close focus viewing from 6 inches to an infinite distance in medical applications includes a single channel uncooled thermal sensor with low noise characteristics and EMI shielding, a remote cable, and a laptop controller with enhanced real time image processing software.

The present disclosure can also be viewed as providing methods of providing a crisp, ultra-sharp, infrared image suitable for medical imaging in a hand carryable package. In this regard, one embodiment of such a method, among others, can be broadly summarized by the following steps: providing a portable, lightweight high-resolution infrared sensor; providing a housing for the infrared sensor, wherein the housing is EMI shielded; and using a processor, displaying an infrared image on a display screen coupled to the sensor.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

These and other objects of the subject invention will be better understood in connection with the Detailed Description in conjunction with Drawings, of which.

DETAILED DESCRIPTION OF THE INVENTION

Figure 1:
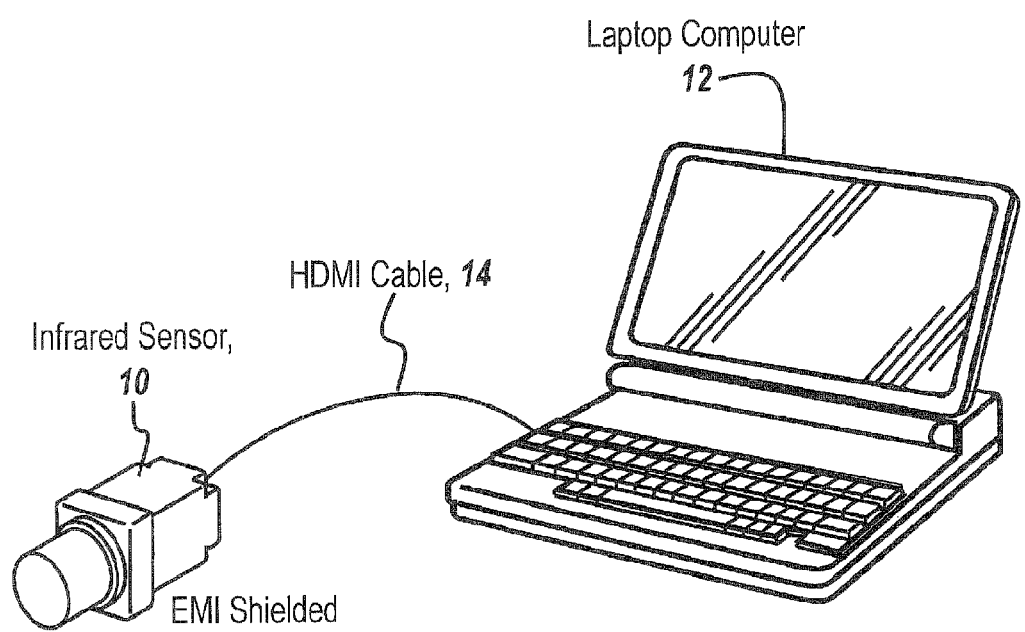
FIG. 1 is a perspective view of a preferred embodiment of the present invention.

The present invention is an apparatus for high resolution single channel thermal imaging in medical applications. The apparatus includes some or all of the following: a highly sensitive EMI shielded thermal imaging device or focal plane array (FPA), a remote cable and laptop controller with real time image processing software. It provides a single viewable IR channel with a variable focus distance which can be optimized at any distance from six inches to infinity. The present invention enables high quality vision in the thermal band for greater awareness of everything within the field of view (FOV) from very close to distant objects and scenes.

Integral to the ability to provide a noise free high quality image is the ability to limit electromagnetic interference. In one embodiment of the subject invention, the sensor housing, hereinafter the camera casing, is divided up into compartments with the joinder of the compartments being provided with EMI shielding therebetween in an annular ridge around the compartments. Moreover, EMI shielding for the rear compartment is provided to seal the connectors that exit the compartment against EMI interference.

The result is an improved infrared sensor which is lightweight, but nonetheless has sufficient EMI shielding to make possible the creation of ultra-sharp infrared images, especially on a laptop to which the sensor is coupled.

According to one related invention (Ser. No. 61/961,745), medical thermal image processing is accomplished by means of using a spatial bandpass and scene based noise suppression filtering, pedestal subtraction and thermal fusion image processing.

Prior art solutions apply a histogram based non-linear transfer function to the image globally or they may apply a variable linear gain and offset function locally. This solution enhances the medically relevant thermal scene information that is revealed to the user.

Due to the highly sensitive IR sensor and at 1-2 ft. of working distance, the system has an increased depth of field of (>6 inches), eliminating the need for autofocus motor controllers and associated complex control algorithms. In one embodiment, five preset filters are provided which are user selectable. The filters can be used individually or in combination and supply processed data in near real time (within 0.1 seconds). These image filters are available to the user via the laptop controller user interface.

It will be appreciated that such a real-time high-resolution infrared imaging system is both portable, low-cost and provides a system by which medical professionals can perform diagnosis and treatment.

For instance, and completely within the doctor's office, one can use the subject device as an aid to Mohs surgery and similar dermatological skin treatments. Moreover, it may be used to discern live tissue from dead tissue in imaging and treatment of skin tags during plastic surgery. Likewise, the subject system can be used as a diagnostic aid during burn treatment such as differentiating between burn classifications. Moreover, the subject device may be used to detect the presence of abdominal aortic aneurysms. The device may also be used, for instance, during brain laser ablation treatment, with faster and more accurate thermal imaging of the dead tissue greatly enhancing the procedure.

Finally, the subject system may be utilized as an adjunctive aid in detecting cardiovascular issues including venal or arterial blockage, frostbite, inflammation, infection or sclerosis.

FIG. 1 is a perspective view of a preferred embodiment of the present invention showing the high resolution IR imaging system. It consists of a 12 micron uncooled, low noise microbolometer focal plane array IR sensor 10, a laptop controller 12 and HDMI signal cable 14. These IR engine systems are based upon 12 micron pitch 640×480 Focal Plane Arrays (FPA). This smaller pitch enables more compact lens designs that provide improved thermal contrast. By adapting the systems for close focus high resolution thermal imaging, a great improvement in the technology and product offering was accomplished.

One aspect of the system design incorporates a single IR channel device which is fully enclosed within a dust/splash/EMI resistant container.

Note, in one embodiment, the IR sensor is powered up using the HDMI cable and has no user controls or interfaces, greatly simplifying the user interface. A manual focus adjustment is provided at the objective lens for coarse adjustment. Due to the highly sensitive IR sensor and at 1-2 ft. of working distance, the system has an increased depth of field of (>6 inches), eliminating the need for autofocus motor controllers and associated complex control algorithms. The IR engine systems described herein involve 12 micron pitch 640×480 Focal Plane Arrays (FPA). This smaller pitch enables more compact lens designs that provide improved thermal contrast. By adapting the systems for close focus high resolution thermal imaging, a great improvement in the technology was accomplished.

More particularly, the subject system design incorporates a single IR channel device which is fully enclosed within a dust/splash/EMI resistant container. The elimination of an autofocus motor controller is a major breakthrough and makes the unit smaller, lighter, more reliable and less expensive.

Figure 2:
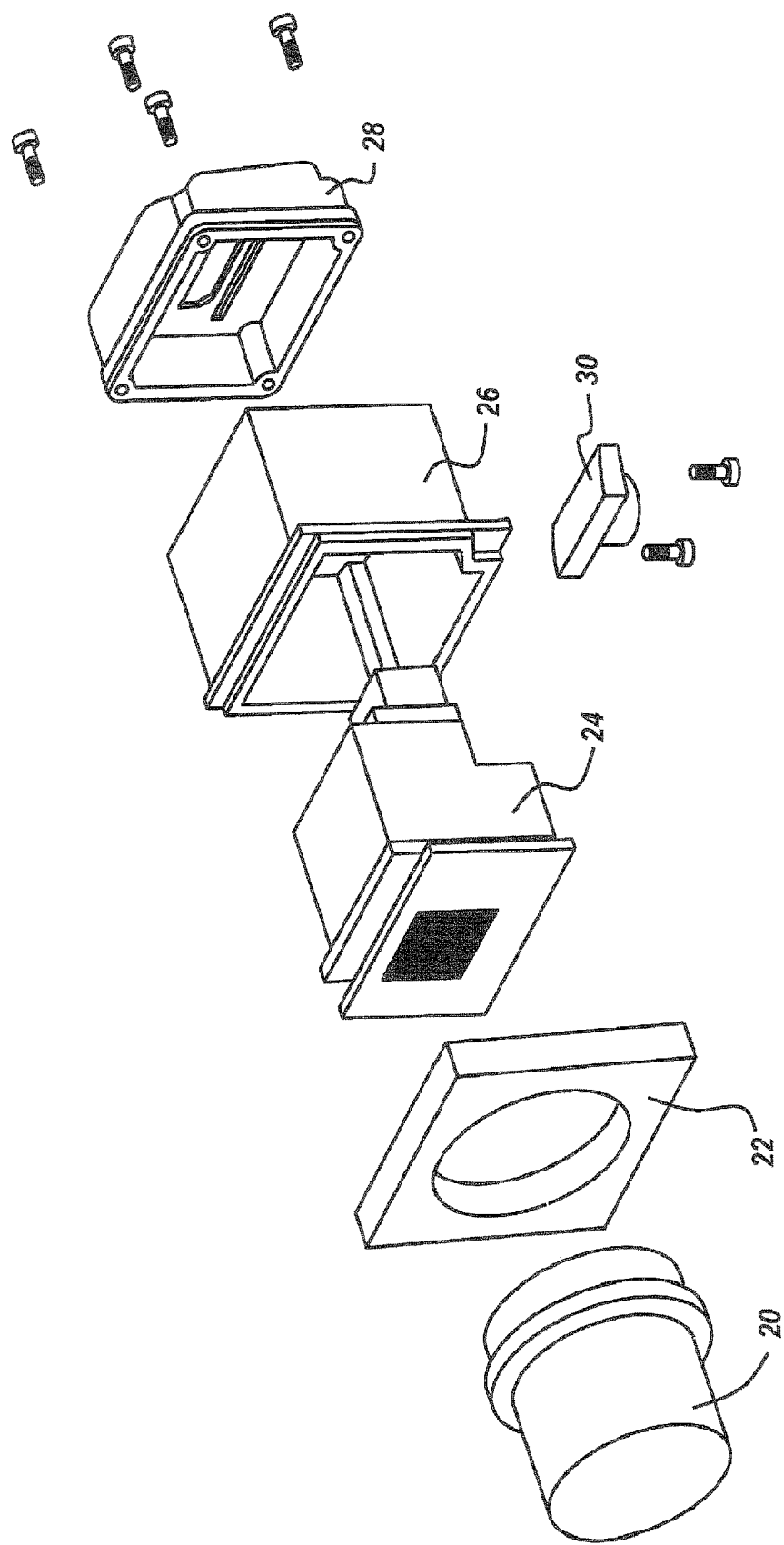
FIG. 2 is an exploded view of high resolution IR sensor as shown in FIG. 1.

FIG. 2 is an exploded view of the high resolution IR sensor as shown in FIG. 1. Referring to FIG. 2, an exploded view of the subject system, which includes the IR sensor is shown. Here it can be seen a camera lens 20 is carried by a front housing 22, which is in turn attached to an FPA assembly 24. This assembly 24 is housed in a mid-housing 26, and a rear housing 28 with a mounting bracket 30, which is provided for convenience.

One of the major features of the subject invention is the EMI shielding that accompanies this very lightweight camera assembly. It will be appreciated that if there is any EMI or noise applied to the HMDI cable, what is presented on-screen is nothing more than a series of horizontal lines quite akin to what is presented on old-fashioned TVs with inadequate antenna systems. Thus, in order to provide a usable portable device, attention must be paid to the camera configuration.

Figure 7:
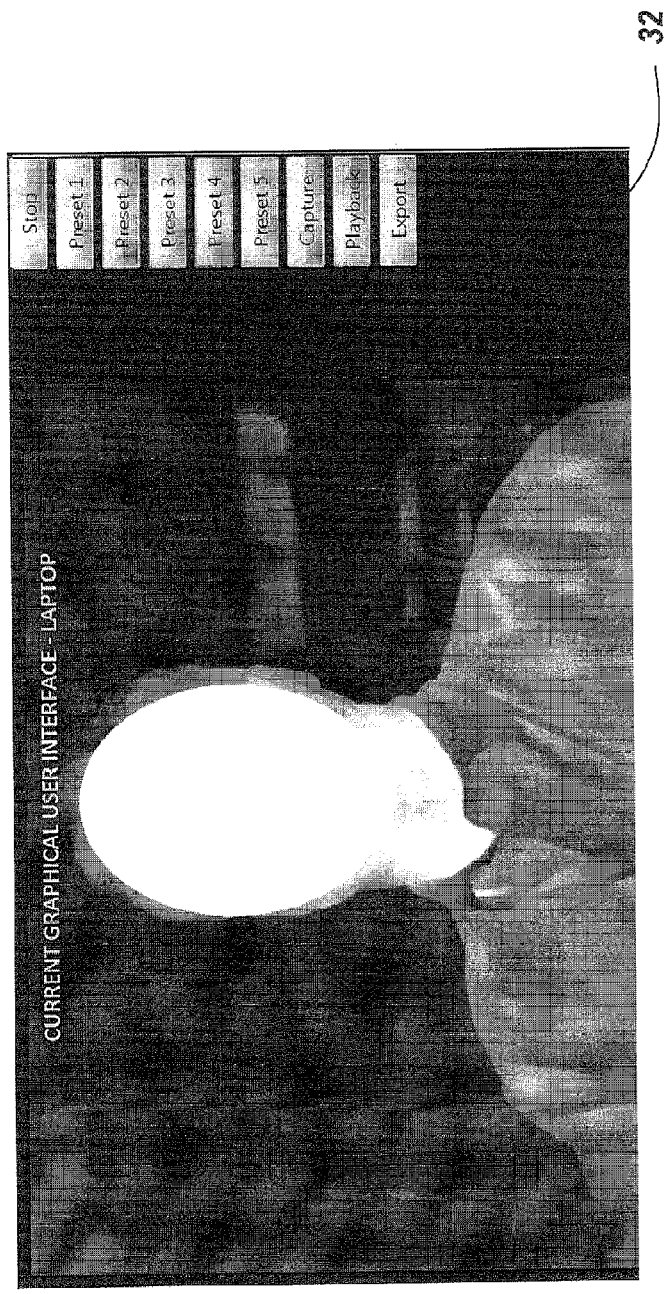
FIG. 7 is an example of Graphical User Interface (GUI) on a laptop computer.

It will be appreciated, due to the high-resolution infrared sensor, that the camera can be focused anywhere from 6 inches to infinity. This permits a lightweight camera to be transported anywhere within, for instance, a medical center and to be able to focus without autofocusing to any object within the focal range of the camera. Features of the camera are as follows:

The laptop controller 12 (FIG. 1) provides a graphical user interface with up to five preset filters which are user selectable for image contrast enhancement. An example of the graphical user output on the laptop computer is shown in FIG. 7, in which camera 10 (FIG. 1) is focused on a human subject a couple of feet from the camera. Here the person being viewed by the subject system is clearly visible, where the detail of the individual's shirt is a testament to the sharpness of the IR image.

The laptop controller 12 is powered either by AC or remote battery, making the system truly portable. The HDMI cable 14 is a standard interface needed for sensor power.

Central to the operability of the subject invention is the housing utilized for the infrared sensor, with the sensor and the housing constituting a camera.

Figure 3:
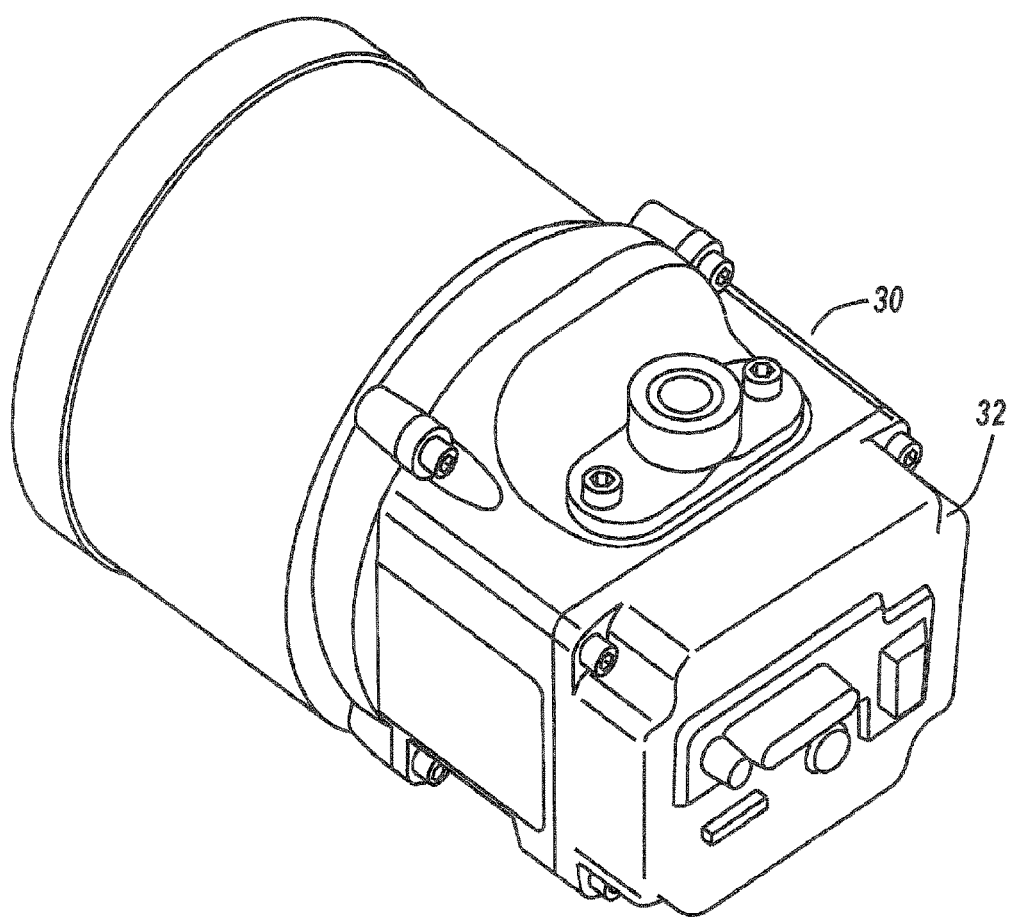
FIG. 3 is a diagrammatic illustration of the rear portion of the infrared sensor of FIG. 1 showing two halves of the casing surrounding electronics, and other parts of the camera.
Figure 4A:
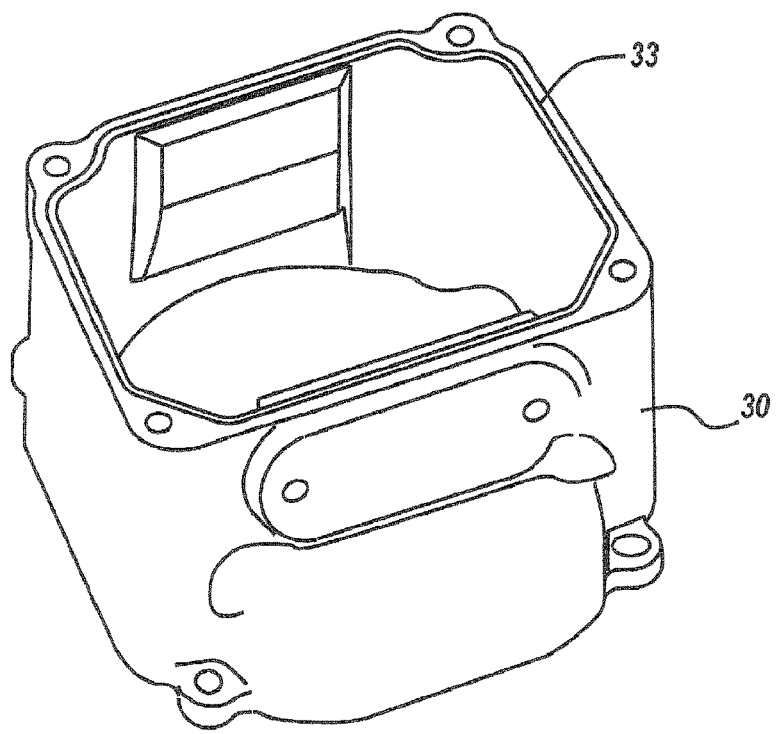
FIG. 4 is a diagrammatic illustration of the two halves of the casing of FIG. 3 shown broken apart, with EMI shielding grooves that mate upon assembly providing for the required EMI shielding.
Figure 4B:
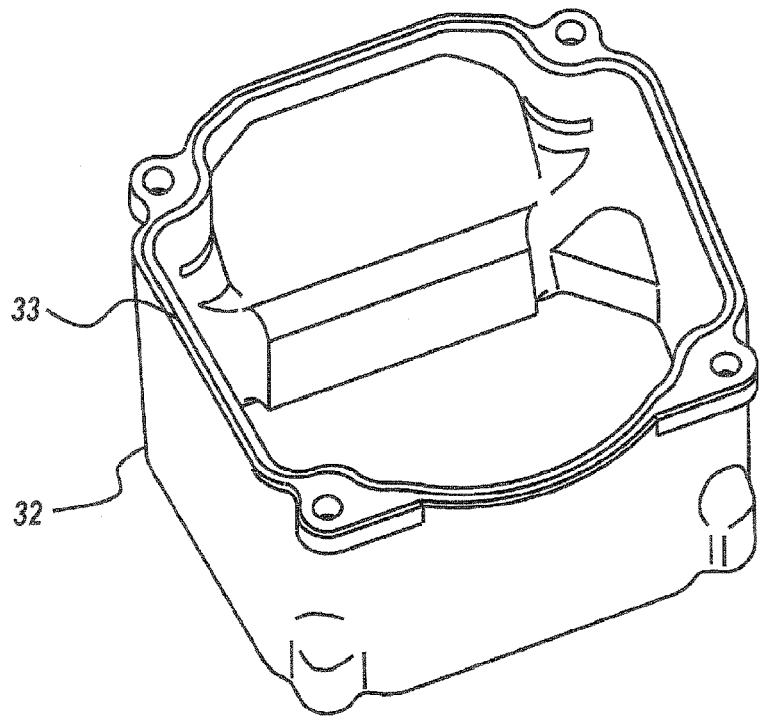

FIG. 3 is a diagrammatic illustration of the rear portion of the infrared sensor of FIG. 1 showing two halves of the casing surrounding electronics, and other parts of the camera. FIG. 4 is a diagrammatic illustration of the two halves of the casing of FIG. 3 shown broken apart, with EMI shielding grooves that mate upon assembly providing for the required EMI shielding. Referring to FIG. 3, what is shown at 30 and 32 are the two halves of a rear facing housing which are secured together. Referring to FIG. 4, housing halves 30 and 32 are provided with EMI sealing grooves 33 containing EMI shielding material, which when the parts of the housing mate, provide for an EMI shield for the camera.

Figure 5A:
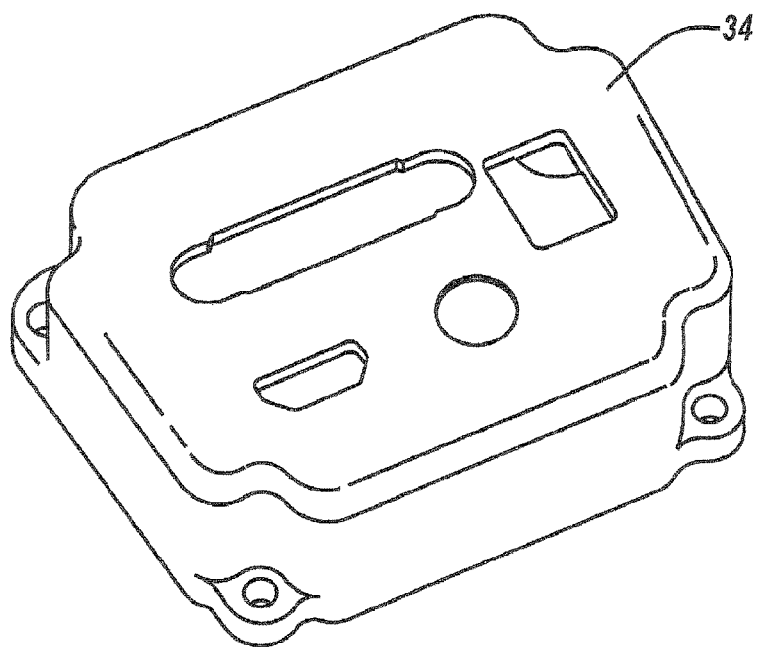
FIG. 5 is a diagrammatic illustration of the rear compartment of the housing for the camera of FIG. 1, illustrating EMI gaskets surrounding the apertures in the housing used for the interconnection of the camera to the laptop of FIG. 1.
Figure 5B:
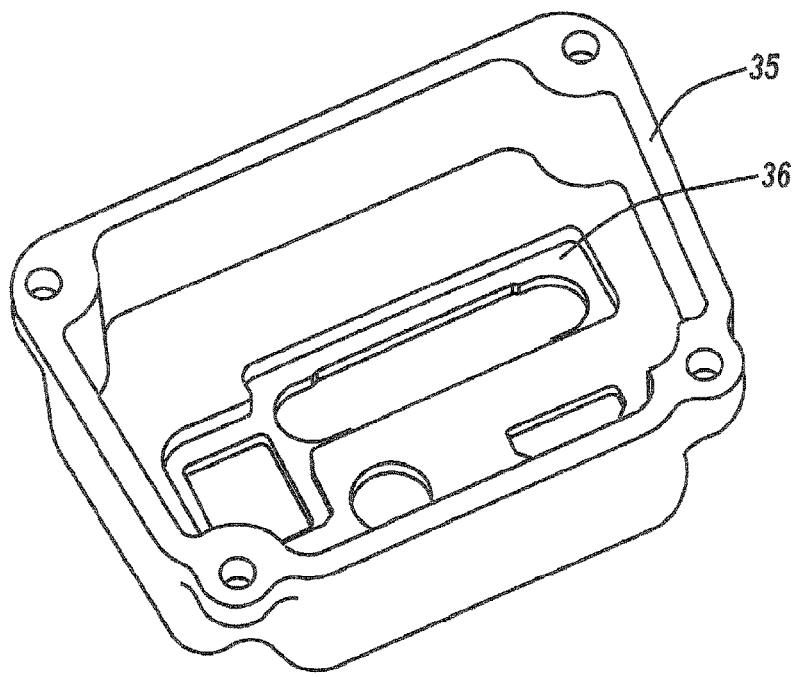

FIG. 5 is a diagrammatic illustration of the rear compartment of the housing for the camera 10 of FIG. 1, illustrating EMI gaskets surrounding the apertures in the housing used for the interconnection of the camera 10 to the laptop 12 of FIG. 1. EMI shielding is further accomplished as illustrated in FIG. 5 by providing a rear cap 34 to the rear of the camera housing, with the top and bottom views shown left and right in this diagram. With respect to the bottom view, apertures 35 are provided with recesses 36 adapted to receive EMI gaskets.

Figure 6:
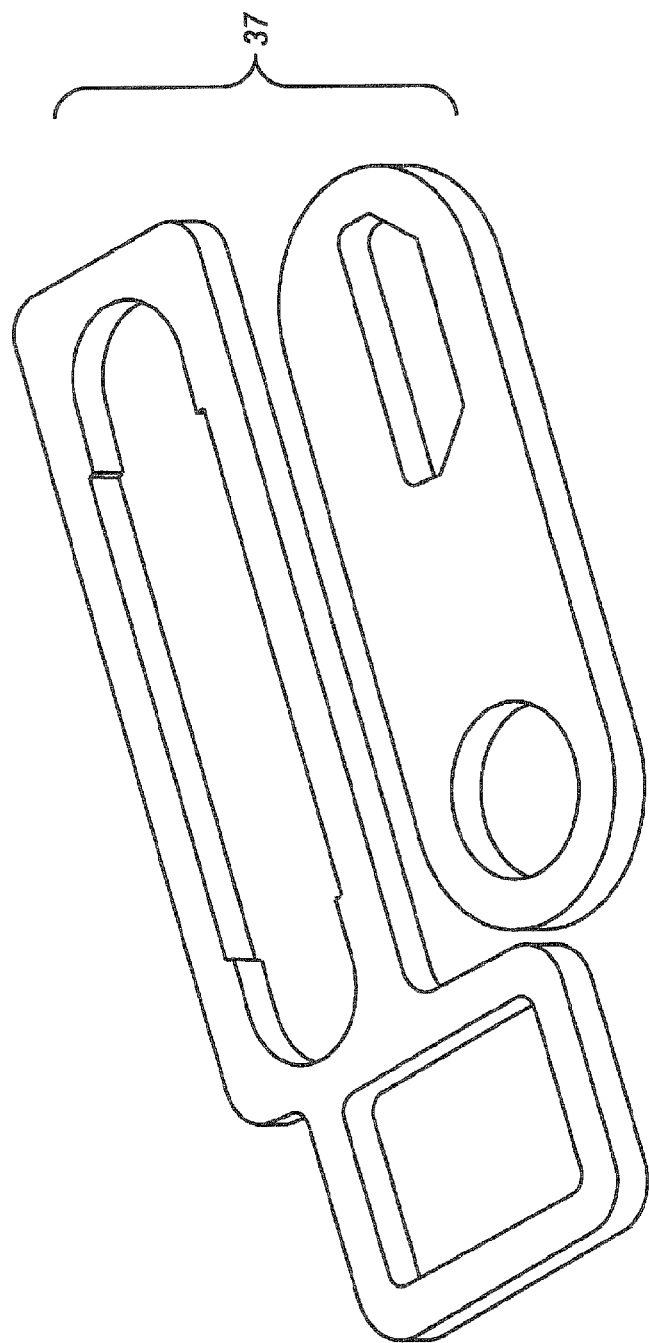
FIG. 6 is a diagrammatic illustration of the EMI gaskets that are fitted into the appropriate orifices in the housing of FIG. 5.

FIG. 6 is a diagrammatic illustration of the EMI gaskets that are fitted into the appropriate orifices in the housing of FIG. 5. Referring to FIG. 6, EMI gaskets 37 are configured as illustrated to fit into the corresponding recesses into the back cap of the camera housing. In this manner, a large portion of electromagnetic interference is removed from interfering with the rendition of the infrared image by the laptop computer.

Post Processing

FIG. 7 is an example of Graphical User Interface (GUI) on a laptop computer. The captured raw IR data is post processed with various suitable image processing algorithms to produce a number of LWIR movies as well as still images 32. FIG. 7 shows an example of a still image 32 after processing with the image processing algorithms. The image processing is described in FIGS. 11-14 hereinafter. It will be noted that five preset filters are provided which are user selectable. The filters can be used individually or in combination and supply processed data in near real time (within 0.1 seconds). These image filters are available to the user via the laptop controller user interface. The logic and description of the methods behind each preset filter is described hereinafter and is disclosed in the related PCT application PCT/US2014/060897 filed Oct. 16, 2014.

To demonstrate the utility of the various image processing techniques in combination, the following examples are presented.

Example 1: Vein Detection

Figure 8:
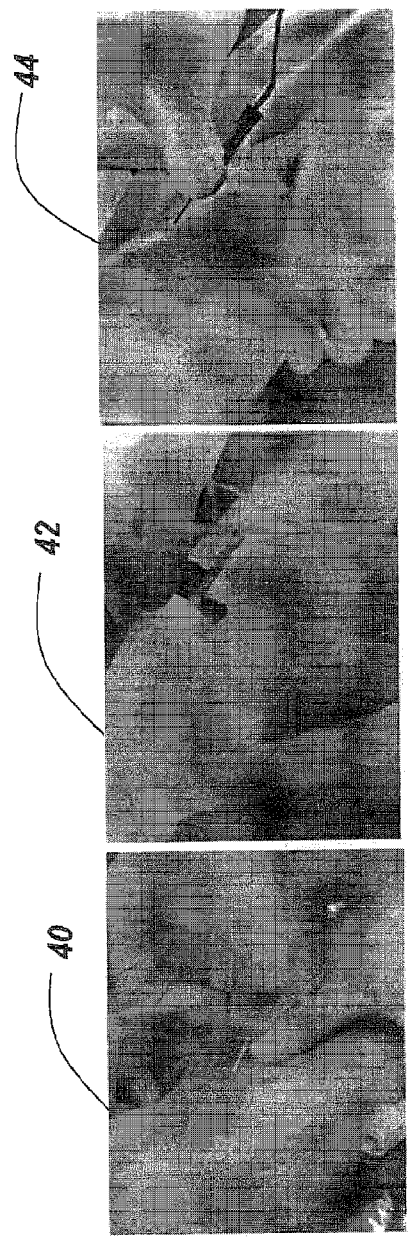
FIG. 8 is an example of high resolution long wave IR output for vein detection.

FIG. 8 is an example of high resolution long wave IR output for vein detection. Referring to FIG. 8, the following comparison images demonstrate significantly more pronounced venous structure of the arm with LWIR imaging over visible imagery. By comparison of the visible image 40 with the unprocessed image 42 and the processed image 44, it can be seen how little evidence exists of vein presence when viewed by the visible eye. "Unprocessed" images refer to raw or original IR output from the FPA sensor. "Processed" images refer to the same original IR output except with real time image enhancement using the software resident on the laptop controller.

Example 2: Hemorrhage Detection

Figure 9:
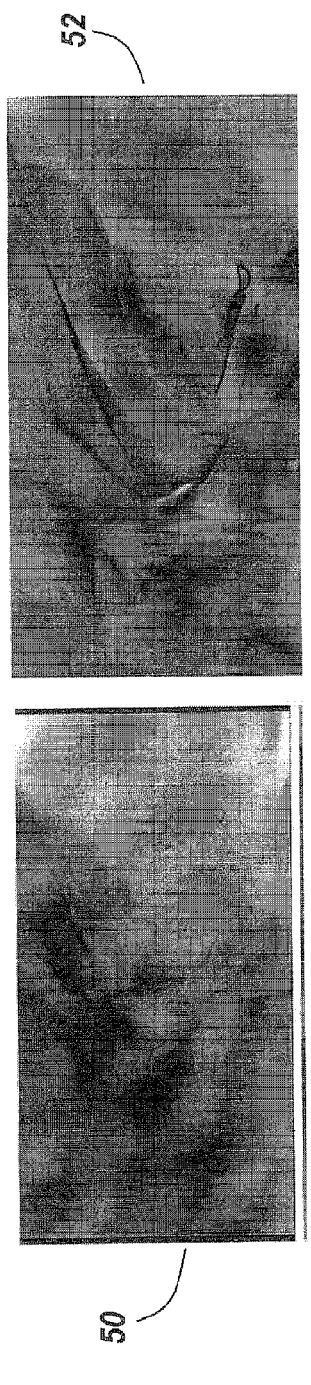
FIG. 9 is an example of high resolution long wave IR output for hemorrhage detection.

FIG. 9 is an example of high resolution long wave IR output for hemorrhage detection. Referring to FIG. 9 and during knee cap surgery, accidental nicking of blood vessels sometimes can occur. This causes the procedure to stop and the surgeon to have to irrigate the treatment, cauterize and restart the procedure. Using high resolution IR imagery, the procedure can be shortened due to increased visibility of the damaged blood vessel area as illustrated in unprocessed form at 50 and processed form at 52.

Example 3: Bone Deburring Heat

Figure 10:
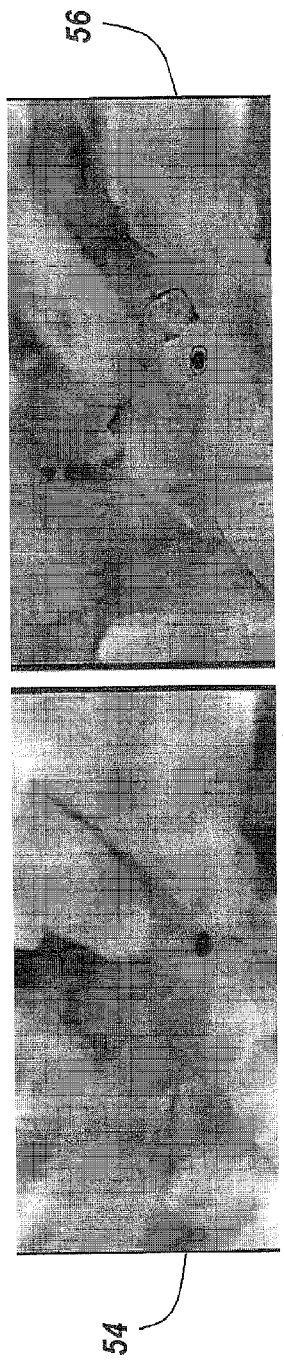
FIG. 10 is an example of high resolution long wave IR output for bone temperature monitoring.

FIG. 10 is an example of high resolution long wave IR output for bone temperature monitoring. Referring to FIG. 10, the same can be said for bone marrow temperature monitoring as shown at 54 for the unprocessed image and at 56 for the processed image. Note the increased image quality of the IR image after image enhancement. Note also that bone temperature rises sharply in a deburring procedure as can be seen in the thermal image in FIG. 10. The monitoring of potentially damaging excessive bone heating is possible through the use of the subject LWIR thermal imaging camera with image processing.

By way of further description and referring to FIGS. 11-14, in one embodiment of the present invention, medical thermal image processing for vein, bone, or other subsurface element detection is accomplished by using a special bandpass and scene-based noise suppression filtering, pedestal subtraction, and thermal fusion image processing system. While prior art solutions apply a histogram-based, nonlinear transfer function to the image globally, or they may apply a variable linear gain and offset function locally, these solutions have not substantially enhanced the relevant thermal scene information revealed to the user.

On the other hand, in the subject system, an infrared camera output is coupled to a spatial band-pass filter having a band limitation such that the high-pass cut-on spatial frequency is equivalent to a radius of 6 to 60 pixels. This configuration limits the input of spatial frequencies to the next step in the scene-based noise suppression system. In one embodiment, spatial noise removal is accomplished by measuring or estimating the spatial noise image contained within the original image followed by subtracting the spatial noise image from the original image. In another embodiment, the scene-based method is used to measure, estimate, or create, and then remove, spatial image noise from the real-time image sequence after an initial delay of a few seconds. After having removed spatial noise, one can consider pedestal subtraction.

Image dynamic range available to the human observer through a display is limited by many factors. Visual perception of a particular object in the scene is improved by utilizing as much of the available display dynamic range as is possible without degrading the dynamic range of other objects in the scene. Display dynamic range must thus be shared between many different scene components. To strike a proper balance, it is necessary to reduce the contrast of large and naturally high contrast scene elements prior to display in order to reserve display dynamic range for small but important scene elements that may be of low contrast in the scene.

Thermal fusion can also be used to emphasize subcutaneous objects. As to thermal fusion, thermal imagery can be viewed as having two types of scene information. The first type of scene information is the size and shape of the various objects in the scene and the second type of scene information is temperature. By combining both size/shape and temperature one can enhance various attributes of objects so they can be readily visualized.

Further enhancements can be achieved by post processing. For example, in one embodiment, the captured 16-bit raw data is post processed with suitable image processing algorithms to produce a number of long-wavelength infrared (LWIR) movies as well as the images appearing herein.

In the subject system, the scene-based noise suppression system has a low spatial frequency noise removal system operating with a spatial band-pass filter frequency equivalent to a radius greater than 60 pixels and up to 480 pixels. The combination of these spatial frequency filters increases the dynamic range and contrast for the objects of interest. The scene-based noise suppression system also has a high-frequency fixed pattern, a slowly varying pattern, or a spatial noise removal system for the removal of unwanted image artifacts which degrade the visual experience of trying to resolve a vein or other subsurface features such as a bone. The spatial band-pass filter in combination with the scene-based noise suppression provides a thermal image processing system that enhances and enables more efficient coupling to the human visual system of the observer of the thermal scene information.

After the thermal image processing, additional enhancement may be obtained through a pedestal subtraction system where a greater portion of the scene dynamic range is efficiently coupled to the observer through the display. Pedestal subtraction reduces the excess dynamic range of large naturally occurring high contrast scene elements, thus enabling smaller, low contrast and important scene elements such as veins to occupy a larger portion of the display dynamic range than would be possible without pedestal subtraction.

Further visualization of the subsurface structure may be provided by a fusion of enhanced thermal elements with non-enhanced thermal elements so as to provide a combined thermal fusion image processing system which utilizes the shape of the subsurface element and its relative temperature in order to be able to distinguish the particular subsurface artifact or structure. In the thermal fusion image processing system, care is taken to keep all parts of the image out of saturation so that vein structure and bone structure can be easily viewed, not only for its position and shape but also for its color, all of which correlates to its temperature.

Unsharp masking may also be utilized in which the unsharp masking technique utilizes an unusually large radius of 7 to 70 pixels to enhance a wide range of medium to high-spatial frequency features that make the subsurface structures more visible and distinguishable from the low-frequency thermal background. The processing involved in rendering the image incorporates a real-time full-frame rate system which involves a scene-based method for low-frequency spatial noise removal and dynamic range enhancement in which slowly varying or low-frequency image elements are removed by a spatial band-pass filter that removes the low spatial frequency image components.

The scene-based method for eliminating spatial or fixed pattern noise involves a method for eliminating high-frequency spatial or so-called fixed pattern noise, meaning noise and clutter removal, by removing a high spatial frequency filtered version of the image from the original image. This removal is done in one embodiment by measuring or estimating the spatial or fixed pattern noise within the image and subtracting it from the original image.

A specialized algorithm for removal of the spatial image involves first creating a frame stack "SBN stack" by applying a 3 to 12 pixel radius spatial high pass filter to the previous two or more frames. Secondly, and in parallel, a frame stack "SBN mask stack" is created by thresholding the 3 to 12 pixel radius variance of each of the previous two or more frames. The next step is to remove the residual scene content from each frame in the stack by applying the "SBN mask stack" as a mask to each frame in the "SBN stack". The result is "SBN masked stack." The next step is to create a spatial noise reference image "SBNref image" by computing the stack frame average of the masked stack. The final step is the removal of the spatial noise from each subsequent frame by subtracting the "SBNref image" from each subsequent frame.

After the scene-based method for noise removal, pedestal subtraction is utilized to preserve display dynamic range for small but important scene elements that may be of low contrast in the scene itself. This pedestal subtraction is done by reducing the contrast of large and naturally high contrast scene elements prior to display. The result is to preserve display high dynamic range for small but important scene elements that may be of low contrast.

After pedestal subtraction, thermal fusion is utilized to meld the size and shape of objects with their temperatures such that the combination of the two parameters heightens the visibility of the particular elements so that they may be visualized easily from the display.

In addition to the above enhancements for the display of thermal imaging, post processing in one embodiment captures 16 bit raw data, linearly stretches the 16-bit data of a single frame, and both provides a 16 frame moving average filtration and at the same time increases subject contrast so as to be able to pop out or make more visible the subcutaneous object required. Rather than utilizing thermal cameras which have minimal image processing built-in, namely just enough to be able to produce a linear level image or linear mapping of the thermal scene, in the subject system details in the thermal scene required to be enhanced so as to be easily detectable are provided by thermal image processing systems. These systems utilize spatial band-pass and scene-based noise suppression filtering as well as pedestal subtraction, thermal fusion image processing and unsharp masking.

Figure 11:
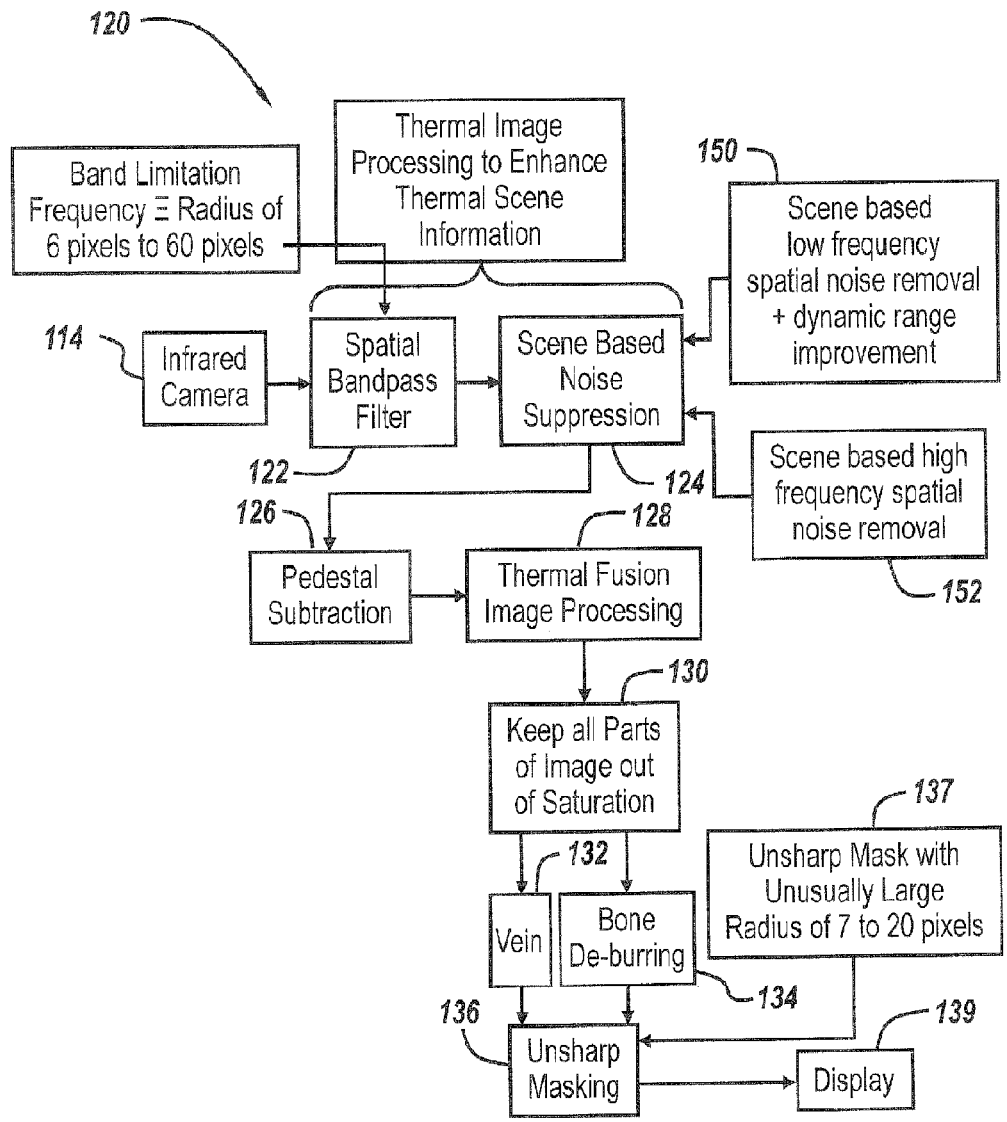
FIG. 11 is a flow schematic diagram of the infrared imaging system in which the infrared camera is coupled to a spatial band-pass filter, a scene-based noise suppression module, a pedestal subtraction unit and a thermal fusion image processing system, followed by unsharp masking to be able to exaggerate or enhance subsurface objects such as veins or bone burrs, in accordance with the first exemplary embodiment of the present disclosure.

This having been said, what is now described is one method for IR filtering, processing and post processing with the infrared signals processed to provide ultra-sharp images. FIG. 11 is a flow schematic diagram of the infrared imaging system in which the infrared camera is coupled to a spatial band-pass filter, a scene-based noise suppression module, a pedestal subtraction unit and a thermal fusion image processing system, followed by unsharp masking to be able to exaggerate or enhance subsurface objects such as veins or bone burrs. Specifically, FIG. 11 schematically illustrates the infrared imaging system in which the infrared camera 114 is coupled to a spatial band-pass filter 122, a scene-based noise suppression module 124, a pedestal subtraction unit 126 and a thermal fusion image processing system 128, followed by unsharp masking to be able to exaggerate or enhance subsurface objects such as veins or bone burrs. As is shown in this figure, the thermal image processing system 120 takes the output of infrared camera 114 and couples it to a spatial band-pass filter 122 that is, in turn, coupled to a scene-based noise suppression unit 124. The output of the scene-based noise suppression unit 124 is coupled to a pedestal subtraction module 126. The pedestal subtraction unit 126 may be used to preserve as much of the available display dynamic range as possible by reducing contrast of large and naturally high contrast scene elements, thus to be able to visualize small low contrast scene elements.

The output of the pedestal subtraction module 126 is coupled to a thermal fusion image processing module 128. The output of thermal fusion image processing module 128 is controlled at saturation controller 130 to keep all parts of the image out of saturation, such that veins or bone de-burring structures are visible, as indicated by boxes 132 and 134. The resulting output of the thermal fusion image processing module 128 is passed through an unsharp masking module 136 to remove noncritical artifacts in the infrared camera output. Unsharp masking module 136 is under control of control unit 137 which restricts the unsharp masking to using an unusually large radius of 120 pixels. Thereafter, the results are displayed on a display 139.

The scene-based noise suppression module 124 may include two different types of noise suppression systems. The first type utilizes a low-frequency spatial noise removal system 150 in which spatial noise of a low-frequency nature is removed which simultaneously improves the dynamic range for those small indistinct subsurface elements of interest. The second type of system used by the scene-based noise suppression module 124 is a scene-based high-frequency spatial noise removal module 152 which removes high-frequency spatial noise.

Figure 12A:
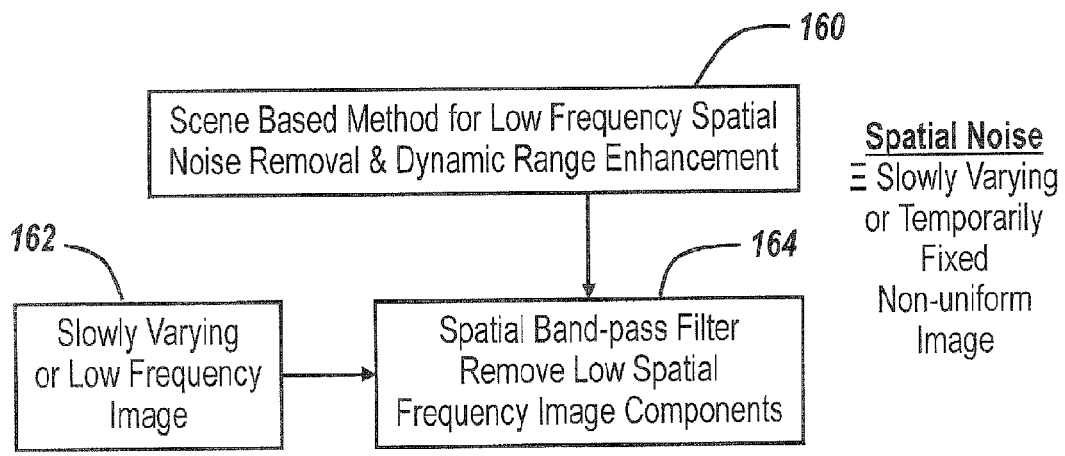
FIG. 12A is a diagrammatic illustration of real time full frame image processing for both low-frequency spatial noise removal and dynamic range enhancement, in accordance with the first exemplary embodiment of the present disclosure.
Figure 12B:
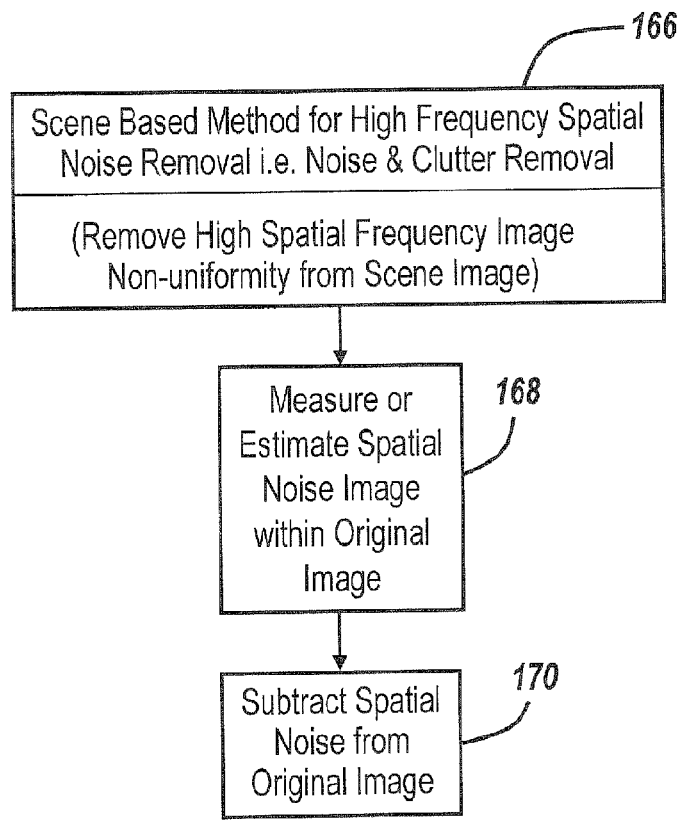
FIG. 12B is a diagrammatic illustration of real time full frame image processing for scene-based methods for high-frequency spatial noise removal including clutter, in accordance with the first exemplary embodiment of the present disclosure.

FIG. 12A is a diagrammatic illustration of real time full frame image processing for both low-frequency spatial noise removal and dynamic range enhancement. FIG. 12B is a diagrammatic illustration of real time full frame image processing for scene-based methods for high-frequency spatial noise removal including clutter. While FIG. 12A illustrates the real time full frame image processing for both low-frequency spatial noise removal and dynamic range enhancement, FIG. 12B illustrates the basics of the real-time full-frame image processing available for scene-based noise suppression. As illustrated at block 160, the scene-based method for low-frequency spatial noise removal and dynamic range enhancement starts off with slowly varying or low-frequency images within block 162. The slowly varying or low-frequency images of block 162 may be applied to a spatial band-pass filter at block 164 to remove low-frequency spatial image components.

As is shown in FIG. 12B, the method provides for removal of high-frequency spatial elements to permit noise removal and thus clutter as well. The method includes removal of high-frequency spatial image non-uniformity from the scene image at block 166. Next, at block 168, the spatial noise image within the original image is measured or estimated. At block 170, the spatial noise is then subtracted from the original image. In either FIG. 12A or FIG. 12B, spatial noise may refer to the slowly varying or temporarily fixed non-uniform images within the scene.

Figure 13:
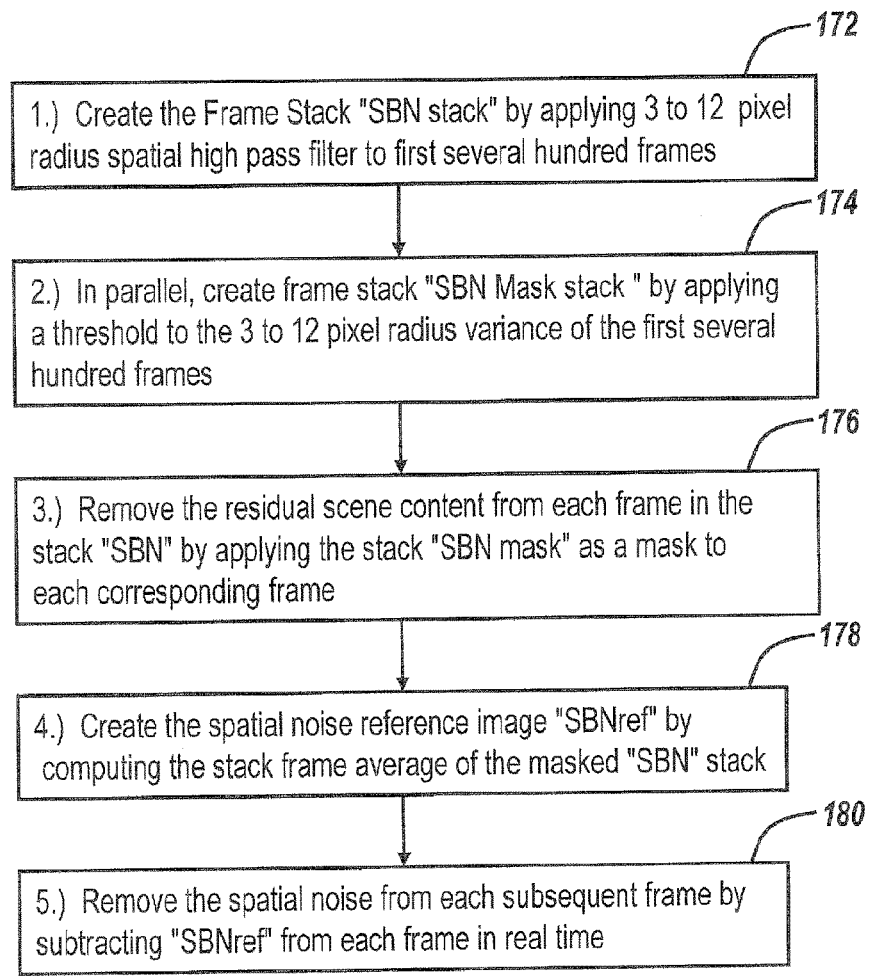
FIG. 13 is a flowchart showing method steps for removal of spatial noise, in accordance with the first exemplary embodiment of the present disclosure; and, FIG. 14 is a diagrammatic representation of the use of pedestal subtraction, thermal fusion and post processing to increase the contrast invisibility of small subsurface objects, in accordance with the first exemplary embodiment of the present disclosure.

FIG. 13 is a flowchart showing method steps for removal of spatial noise, in accordance with the first exemplary embodiment of the present disclosure. In order to remove spatial noise, the frame stack SBN stack is created by applying a 3 to 12 pixel radius spatial high pass filter to the first several hundred frames, as is shown at block 172. The frame stack SBN mask stack is then created, in parallel, by applying a threshold to the 3 to 12 pixel radius variance of the first several hundred frames, as is shown at block 174. The residual scene content from each frame in the stack SBN is removed by applying the stack SBN mask as a mask to each corresponding frame, as is shown at block 176. The spatial noise reference image "SBNref" is then created by computing the stack frame average of the masked SBN stack, as is shown at block 178. Spatial noise is then removed from each subsequent frame by subtracting the "SBNref image" from each frame in real time, as is shown at block 180.

Figure 14:
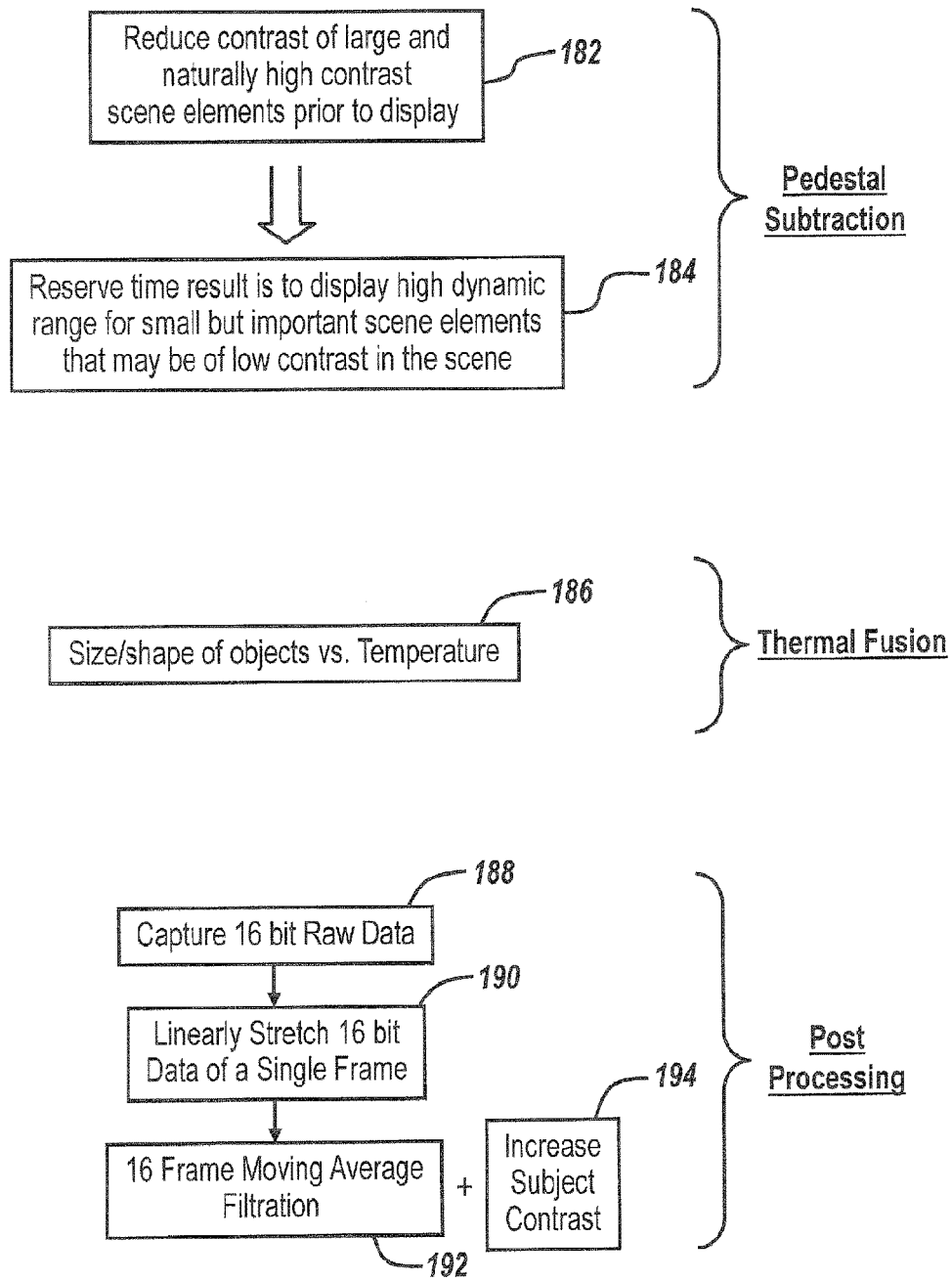

Removal of scene-based noise as well as providing a spatial band-pass filter improves the enhancement of the subsurface objects within the human anatomy. However, further enhancements may be obtained by utilizing a technique called pedestal subtraction. FIG. 14 is a diagrammatic representation of the use of pedesal subtraction, in which thermal fusion and post processing are used to increase the contrast visibility of small subsurface objects. As is seen in FIG. 14, pedestal subtraction may allow displaying a high dynamic range for small, but important scene elements that may be of low contrast in the scene. Pedestal subtraction may include reducing contrast of large and naturally high contrast scene elements prior to display, as is shown at block 182. Reducing contrast may then allow for reserving a time result to display the high dynamic range for the small but important scene elements that may be of low contrast, as is shown at block 184.

Next, using a process of thermal fusion, two different types of information may be taken into account in order to display the subsurface object, as is shown at block 186. The first type is the size or shape of the object as well as its location and the second type is its temperature. By displaying these two simultaneously one can enhance the features that are sought after, especially small subsurface objects which are not generally high contrast can be seen.

Subsequently, at post processing, further enhancements can be obtained. As is shown at block 188, 16 bit raw data may be captured. Thereafter, as shown at block 190, the 16 bit data is linearly stretched corresponding to the stretching of a 16-bit data of a single frame. Next, a 16 frame moving average filtration may be used simultaneously with a system for increasing the contrast of the object sought after, as is shown at block 192 and block 194, respectively.

What is therefore shown is a system for enhancing thermal imaging to be able to visualize and enhance subsurface objects within a human or mammalian context in which thermal imaging cameras can be used with enhanced techniques to be able to make visible various small and non-contrasted features that lie beneath the surface of the skin. All of the above is made possible by the use of EMI shielding in a specialized camera body or housing as described above.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A device for high definition thermal imaging and close focus viewing from 6 inches or more distance in medical applications, said apparatus comprising:
   a single channel uncooled thermal sensor with low noise characteristics and EMI shielding;
   a remote cable; and
   a laptop controller with enhanced real time image processing software providing thermal image processing of an output of the uncooled thermal sensor to provide thermal scene information, wherein the thermal image processing includes a spatial bandpass filter and a scene based noise suppression system for removing low frequency spatial noise and high frequency spatial noise, wherein the enhanced real time image processing software is used as an aid for at least one of:
   detecting a presence of abdominal aortic aneurysms;
   differentiating between burn classifications during burn treatments;
   assisting Mohs surgery and dermatological skin treatments; and
   detecting cardiovascular issues including at least one of: venal blockage, arterial blockage, frost bite, inflammation, infection, and sclerosis.

2. The device of claim 1, wherein the enhanced real time image processing software further comprises an imperceptible amount of delay in a displayed image, wherein the imperceptible amount of delay is less than 0.1 seconds.

3. The device of claim 1, wherein the enhanced real time image processing software is used to discern live tissue from dead tissue in an imaging of skin tags during plastic surgery.

4. The device of claim 1, wherein the enhanced real time image processing software is used during brain tumor laser ablation treatment for thermal imaging of dead tissue.

5. The device of claim 1, wherein the sensor is a 12 micron sensor.

6. The device of claim 1, wherein the sensor has a pixel spacing from 10 microns to 17 microns.

7. The device of claim 1, wherein said sensor has a housing including a pair of co-joined portions and EMI shielding placed between said co-joined portions.

8. The device of claim 7, wherein said pair of co-joined portions further comprises an end, wherein the end has apertures there through and recesses surrounding said apertures, further comprising an electromagnetic interference reducing material in said apertures.

9. The device of claim 8, wherein said apertures house connectors to said sensor through said end at a point at which electromagnetic interference reducing material is present.

10. The device of claim 1, wherein the scene based noise suppression system further comprises a low-frequency spatial noise removal system.

11. The device of claim 1, wherein the scene based noise suppression system further comprises a scene-based high-frequency spatial noise removal module.

12. The device of claim 1, wherein the output of the uncooled thermal sensor is high resolution long wave IR.

13. The device of claim 1, further comprising a pedestal subtraction unit and a thermal fusion image processing system.

14. A method for providing a crisp, ultra-sharp, infrared image suitable for medical imaging in a hand carryable package comprising the steps of:
   providing a portable, lightweight high-resolution infrared sensor;
   providing a housing for the infrared sensor, wherein the housing is EMI shielded;
   using a processor, displaying an infrared image on a display screen coupled to the sensor; and
   executing post processing algorithms with the processor for processing an output of the infrared sensor to provide the displayed infrared image, further comprising thermal image processing to enhance thermal scene information, wherein the thermal image processing includes a spatial bandpass filter and a scene based noise suppression system for removing low frequency spatial noise and high frequency spatial noise.

15. The method of claim 14, further including thermal fusion image processing and a system for keeping all parts of the displayed image out of saturation.

* * * * *